United States Patent [19]

Suroff

[11] 4,040,414
[45] Aug. 9, 1977

[54] ULTRASONIC PERSONAL CARE INSTRUMENT AND METHOD

[75] Inventor: Leonard W. Suroff, Jericho, N.Y.

[73] Assignee: Xygiene, Inc., Panama, Panama

[21] Appl. No.: 685,518

[22] Filed: May 12, 1976

[51] Int. Cl.² .............................................. A61H 1/00
[52] U.S. Cl. .................................. 128/24 A; 128/276
[58] Field of Search ...................... 128/24 A, 276, 355, 128/275, 260

[56] References Cited

U.S. PATENT DOCUMENTS

| 3,352,303 | 11/1967 | Delaney | 128/24 A |
| 3,874,372 | 4/1975 | Le Bon | 128/24 A |
| 3,941,122 | 3/1976 | Jones | 128/24 A |

*Primary Examiner*—Lawrence W. Trapp

[57] ABSTRACT

The invention relates to the field of hygienic care of the human skin and for performing certain dermatological procedures as removing blackheads and opening pimples with an ultrasonic applicator. The applicator or tool, which is used in conjunction with a selected fluid, has a contoured configuration or surface that is placed in energy transmission relationship to the skin and ultrasonically vibrated for performing the particular procedure desired.

79 Claims, 17 Drawing Figures

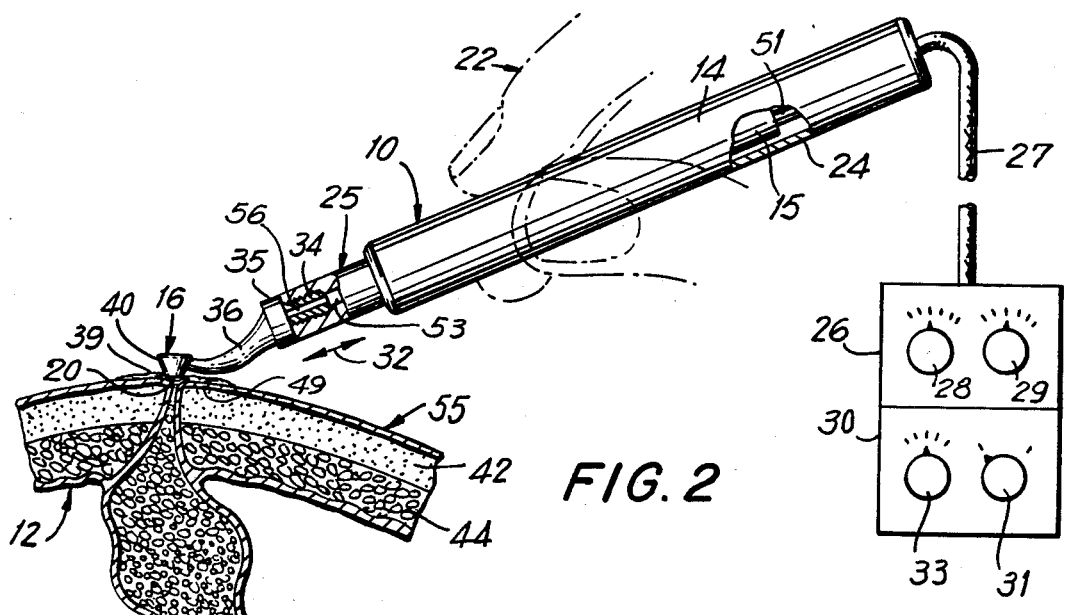
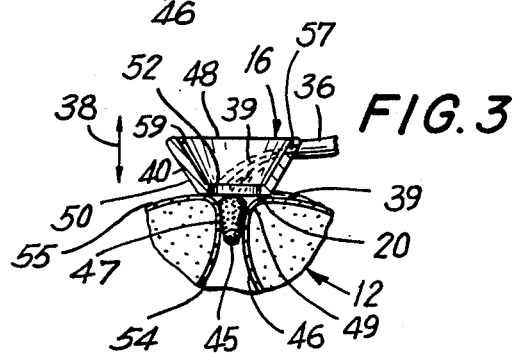
FIG. 2
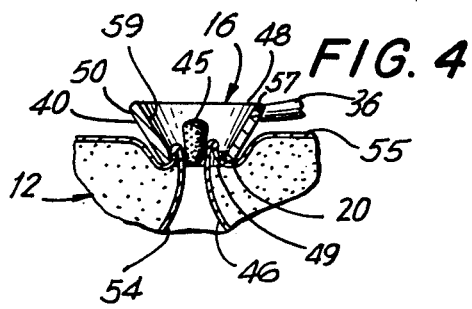
FIG. 3
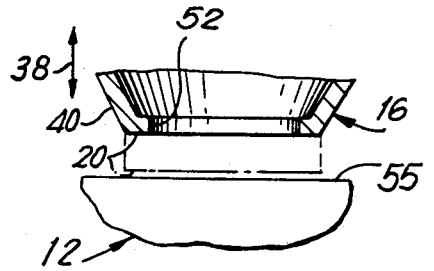
FIG. 6
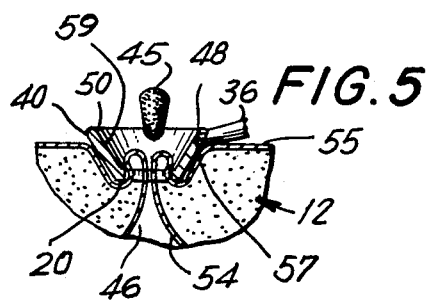
FIG. 5

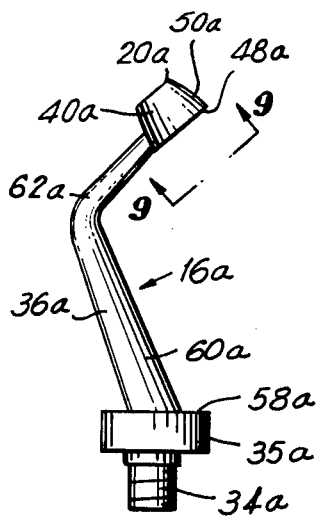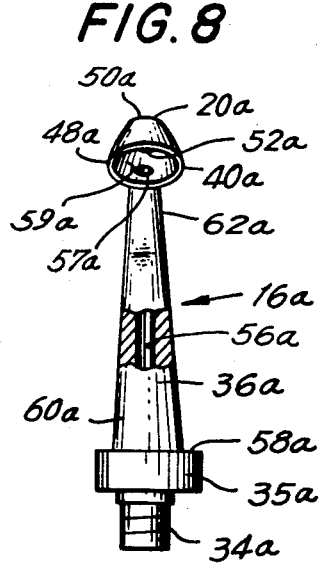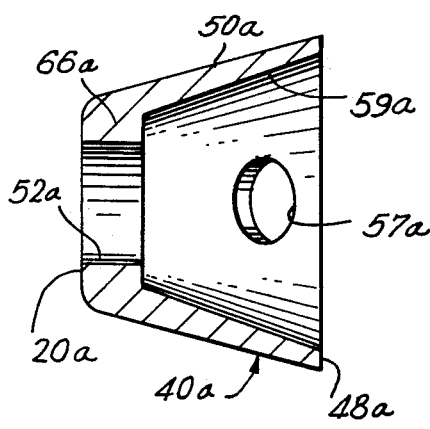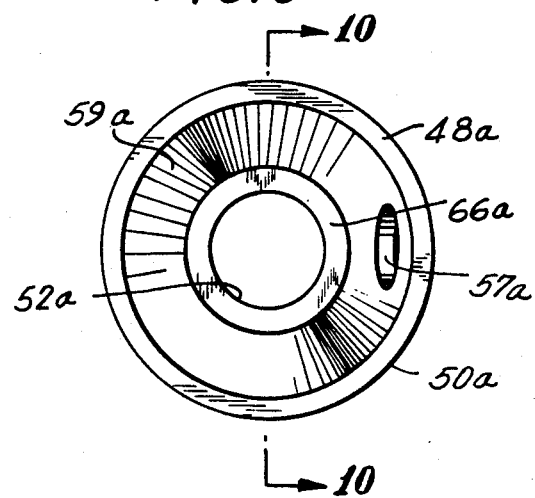

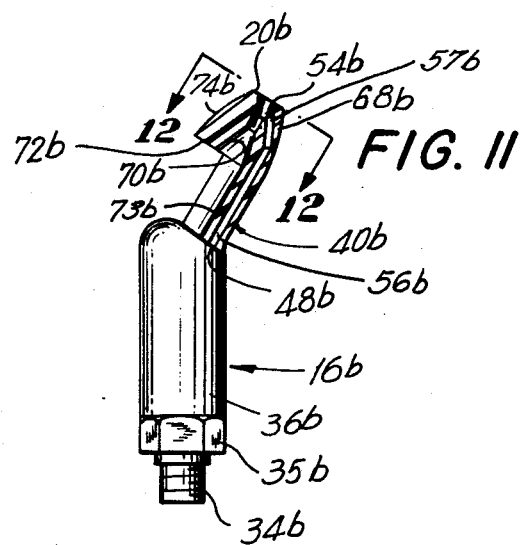
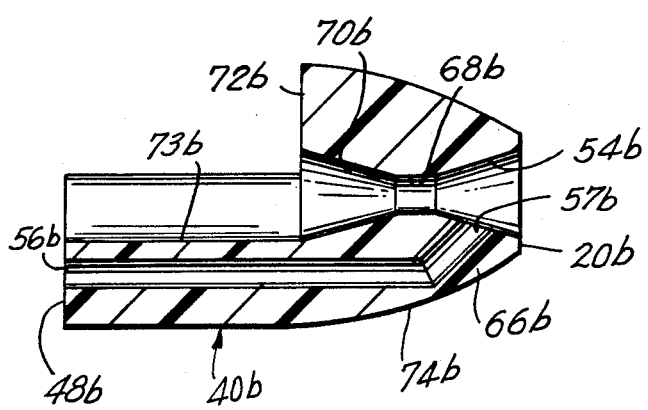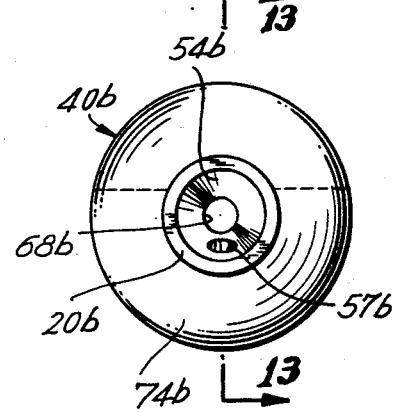

ULTRASONIC PERSONAL CARE INSTRUMENT AND METHOD

BACKGROUND OF THE INVENTION

This invention relates generally to the personal care of humans, and more particularly, to methods and apparatus utilizing ultrasonic vibratory energy for removal of foreign substances such as blackheads from the skin, and the treatment of pimples.

This invention deals with the discoveries made when using an ultrasonic motor with a plastic or metallic output head to remove blackheads and to express the pus from pimples. The underlying principle is an application of the broad thermal equivalence principle, which recognizes that it is possible, through the use of mechanical high frequency vibrations in coherent form to accomplish results which otherwise require the use of elevated temperatures, which latter is equivalent to using mechanical high frequency vibrations in coherent form.

The present invention involves the use of ultrasonic mechanical vibrations in conjunction with various fluids that obtain a lowering of the viscosity of either the sebaceous contents of a blackhead, or the whitish pus matter in a pimple. At the same time, the output contour of the ultrasonic tool is so fashioned that a gentle static pressure exerted against the skin around a blackhead or pimple is transmitted through the surrounding tissue into the region containing the matter to be expressed (i.e, pushed out), and a fluid ideally suited for the particular application is used in conjunction therewith.

There are a number of problems here, and some background is needed to understand the benefits which accrue from the subject invention. In the first place, ordinary methods of removing blackheads or squeezing pimples requires the use of a squeezing force which reddens and bruises the surrounding tissue. This is not only uncomfortable, but it also leaves a mark on the skin which it takes some time to heal or subside. A device which materially lessens or removes this undesirable effect is a definite and important advance in this dermatological art.

OBJECTS OF THE INVENTION

An object of the invention is to provide improved methods and apparatus for performing personal care procedures with ultrasonic energy.

Another object of the invention is to provide novel and improved cleaning techniques for personal care which enables the user to control and obtain significantly better removal of blackheads.

Another object of the present invention is to provide novel and improved cleaning techniques using medicinal and other fluids for personal care which enables the user to control and obtain significantly better opening of pimples.

Another object is to provide new and novel methods and apparatus which are embodied in a device that is completely safe for use in the home on a regular basis.

Another object of the present invention is to provide new and novel methods and apparatus for regular personal care which provides excellent results and simultaneous stimulation.

Another object of the present invention is to provide improved cleaning techniques for the removal of blackheads, pimples and other skin foreign deposits.

Other objects and advantages of this invention will become apparent as the disclosure proceeds.

SUMMARY OF THE INVENTION

The outstanding and unexpected results obtained by the practice of the method and apparatus of this invention are attained by a series of features, steps and elements assembled working together in inter-related combination.

The present invention is utilized by vibrating an applicator having certain characteristics to effect a transmission of high frequency mechanical vibration for performing home and professional personal care by the user. The applicator is generally applied against the skin in the field of a fluid medium. The fluid medium may be selected to perform a variety of functions, as to both flush away the removed foreign material and act as a coupling agent as well as to provide a cooling action. The fluid may also be medicinal in nature to sterilize the work site, act as an anaesthetic, etc.

Specifically, a hand held applicator of plastic or other material, in an elongated slim shape and containing incorporated removing means attached to a high frequency mechanical vibratory motor is disclosed.

The present invention makes use of the kilohertz range of frequency, from one thousand to several hundred thousand reciprocations per second, and its special characteristics. In the first place, kilohertz energy is readily transmitted through animal tissues with relatively small absorption compared with the higher or megahertz range of ultrasonic energy. This is a very important point because it indicates the inherently safer aspect of kilohertz energy, which, in fact, includes the sonic range of frequency.

In the second place, the ultrasonic motor produces an output reciprocal motion characterized by a kilohertz frequency coupled with a reciprocating stroke measured in thousandths of an inch. All the mechanical parameters of the motor may be expressed in terms of these two basic parameters; i.e., frequency, $f$, on the one hand and maximal stroke, $s$, on the other. Simple computation based on a given $f$ and $s$, shows at once that the ultrasonic motor output is unique in that, with an invisible, microscopic motion, it produces a peak speed which is quite low (i.e., in the range of 10 miles per hour), combined with a peak acceleration which is in the range of tens of thousands times the acceleration of gravity. This combination of mechanical parameters cannot be produced by any other source of energy, and is therefore the unique characteristic of the ultrasonic motor, whereby it produces its whole range of unique effects.

For personal care applications, it is difficult to give a detailed account of all the effects possible to the above combination of mechanical factors in the output of an ultrasonic motor, but it is possible to list some of the better known implications of these factors. First of all, the enormous peak acceleration of the output element of the motor should be considered.

Classical dynamics, through Newton's Second Law of Motion, requires that a force is necessary to cause a mass to acquire or maintain an acceleration. The quantitative relation is quite simple:

1. (FORCE) $F$ = (MASS) $m$ x (ACCELERATION) $a$

It is clear from this equation that a large force is necessary to produce a very high acceleration in any mass, $m$. It therefore follows that in order to get the mass of the output end of an ultrasonic motor to reciprocate tens of thousands of times per second and during each reciprocation to experience a peak acceleration as high as say, 50,000g (g = acceleration of gravity), then the motor must generate internal force given by equation (1). This is just what happens, and these high reciprocating forces appear in the motor structures as high reciprocating stresses. In order to withstand these stresses the motor must be designed to accommodate the strains induced by such stresses, without fatiguing and fracturing.

But more important for the user of the motor, the question arises as to what happens when the motor output attempts to transmit such high reciprocating accelerations to the load or object being worked if the motor output tool is pressed with moderate force against this object; i.e., tissue, it will be found that the surface of the object in contact with the tool will not be able to follow the motor reciprocations. Furthermore, if these reciprocations have a significant component perpendicular to this surface, then the tool will withdraw and return to said surface, being out of contact altogether during most of the time of each reciprocation. Deeper reflection on this phenonomen will make it evident that the tool end creates a kind of "zone of motion" not penetrated by the object's surface. Therefore an air film is maintained most of the time between the tool end and the object's surface, resulting in an amazing reduction in friction between the tool surface and the work surface,.

Now, if the applicator or tool of the motor is placed against a solid surface so that the reciprocation remains susbtantially perpendicular to the surface, then, while maintaining the zone of motion of the tool, there will be sufficient energy transmitted to effect a penetration of the skin to open a pimple, remove a blackhead, or induce a penetration of chemicals or medicants into the skin. This effect really represents a new low-speed way of micro-penetration in an object.

So far, it is evident that the tool or working end of an ultrasonic kilohertz motor, when applied to an object, such as skin, is capable of producing many thousands of significant force actions every second at low peak speeds and with invisible strokes. Furthermore, these repetitive actions may be engineered so as to produce either extremely reduced friction or greatly enhanced friction effects depending on how the direction of the motor stroke operates relative to the working surface of the solid.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

FIG. 2 is an enlarged fragmentary section of a portion of a biological organism diagrammatically illustrating the initial aspect of removing a foreign deposit from the skin in accordance with the present invention;

FIGS. 3, 4 and 5 illustrate in a manner similar to FIG. 2, the next sequential steps of removing the foreign deposit, such as a blackhead, from the surface of the skin;

FIG. 6 is an enlarged fragmentary view diagrammatically illustrating the vibration pattern of the system;

FIG. 7 is a side view of the applicator means to be used in accordance with the present invention;

FIG. 8 is an end view of the applicator means illustrated in FIG. 7;

FIG. 9 is an enlarged partial end view taken along the line 9—9 of FIG. 7;

FIG. 10 is an enlarged sectional view of a portion of said applicator means taken along the line 10—10 of FIG. 9;

FIG. 11 is a view similar to FIG. 7 illustrating another form of applicator means;

FIG. 12 is an enlarged partial end view taken along the line 12—12 of FIG. 11;

Fig. 13 is an enlarged sectional view of a portion of said applicator means taken along the line 13—13 of FIG. 12;

DETAILED DISCUSSION OF THE DRAWINGS

The high frequency transducer means may be either in the sonic or ultrasonic frequency range, but for purposes of the present invention the word "ultrasonic" will be used to denote vibrations in the range of approximately 1,000 to 1,000,000 cycles per second. In addition, the term "foreign deposit" as used herein is intended to include any matter either of a type not normally found in the human body, or a growth thereof.

In performing the procedures of the present invention, there are several factors that have to be taken into consideration and anaylzed in terms of a total or effective value to obtain the desired end results. The term "total value" may be defined as the proper combination of these factors to obtain the desired end result.

Figure 1:
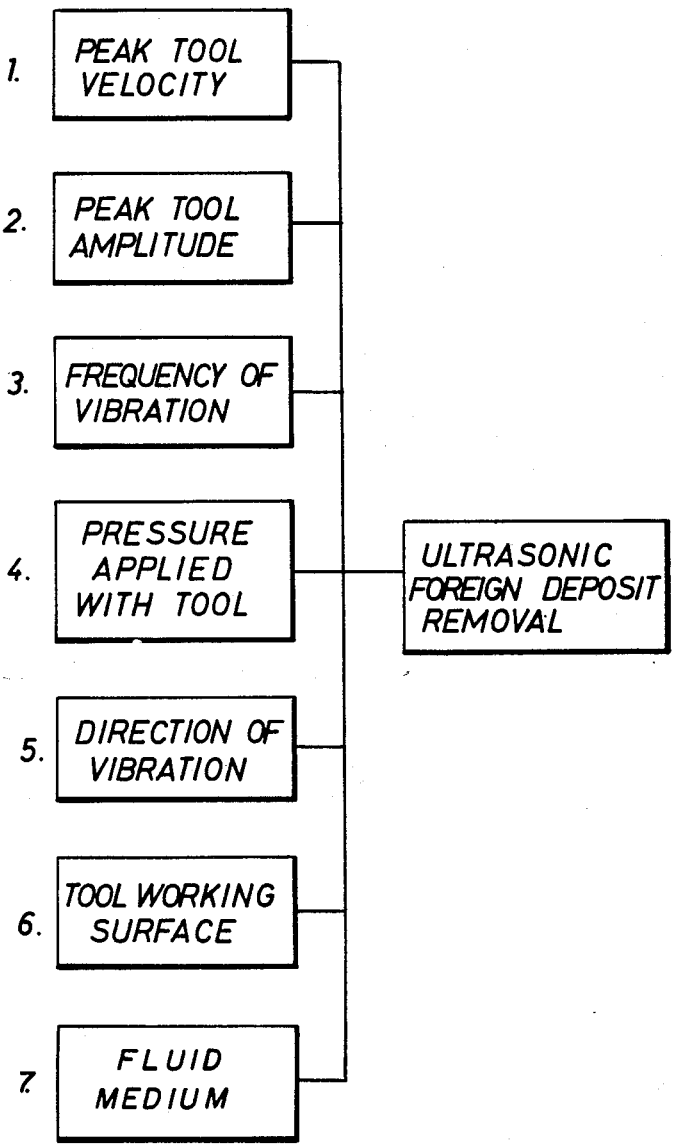
FIG. 1 is a chart indicating the relationship of the principal factors affecting the practicing of the present invention for the removal of foreign deposits.

Referring now to the drawings, in FIG. 1 is a chart illustrating the relationship of the seven principal factors which are involved in whole or in part for determining the total value associated with performing procedures in accordance with the present invention for extracting deposits from layers of human tissue. The related factors are: peak tool velocity, peak tool amplitude, frequency of vibration, pressure applied with tool, direction of vibration, tool working surface, and fluid supply. These factors vary with respect to the procedure being performed.

In the embodiments of the invention discussed below, the working or contacting surface of the applicator means or tool member is placed in engagement with the layer of tissue at a surface thereof such that a small compressive force is applied in a plane substantially normal to the engaged surface. While this compressive force is maintained, the working surface of the tool member is vibrated at an ultrasonic rate to apply an additional energy-producing force at the engaged surface. The compressive and energy producing forces are continued until the foreign deposit is caused to be ejected from its containment within the cavity it is positioned in the body tissue.

When the foreign deposit is within a pimple, the forces are applied to the peripheral surface thereof for producing localized vibratory motion to effect a rupture of the wall thereof with a resultant escaping therefrom. The energy producing force may be divided into (1) mechanical vibration energy absorption in tissue, and (2) friction reduction of the foreign deposit relative to the tissue, both of which result in a localized motion of the foreign deposit relative to the tissue.

Referring again to the drawings, and with respect to FIG. 2, it will be seen that an apparatus 10 for ultrasonically performing procedures on a biological organism, such as a human 12, may include instrument means 14 having an ultrasonic transducer or motor 15 contained therein for effecting the necessary high frequency vibrations of the applicator means or tool member 16, having a contacting surface or output edge 20. The ultrasonic instrument means 14, as illustrated, may be in the form of a driving member adapted for being hand held as by an operator 22, and generally comprising a tubular housing or casing 24, into which coupling means 25 for supporting the applicator means 16 may be partially telescoped. The ultrasonic motor 15 is energized by an oscillation generator 26, with a conduit 27, connecting the two together. The generator is an oscillator adapted to produce electrical energy having an ultrasonic frequency and may have a power control means by knob 28 and frequency adjustment by means of knob 29.

Fluid supply means 30 may be positioned in operative relation to the generator 26 and contain an on-off power switch 31 and a regulator switch 33. The fluid supply means 30 may include pumping means and reservoir means (not shown) therein with the regulator switch 33 controlling the rate of flow that the fluid is dispensed through the pumping means of the fluid supply means 30. The fluid supply means 30 is connected by the conduit 27 in a separate tube contained therein (not shown) to the instrument means 14 for passage therethrough of a fluid 39. The fluid supply means 30 may take various forms and shapes with the end purpose of supplying on a continuous or intermittant basis the fluid 39.

The instrument means 14 may be one of a variety of electromechanical types, such as electrodynamic, piezoelectric and magnetostrictive. The ultrasonic motor for effecting procedures through hand directed tools of suitable configuration, which are readily replaceable or inter-changeable with other work performing tools in acoustically vibrated material treating devices, may be of the type well known in the art.

The generator 26 with the instrument means 14 may be designed such that the applicator means 16 is designed such that a pulsing action occurs simultaneously with the ultrasonic energy. The pulsing of the output edge surface 20 may be at a preselected pattern of pulses at spaced intervals of time in the frequency of from 10 up to 1,000 cycles per second. This further helps the friction reduction effect.

The transducer in the ultrasonic motor 15 is longitudinally dimensioned so as to have lengths which are whole multiples of half-wavelengths of the compressional waves established therein at the frequency of the alternating current supplied so that longitudinal loops of motion as indicated by arrow 32, occur at the coupling means 25. Thus, the optimum amplitude of longitudinal vibration and hyper-accelerations of applicator means 16 is achieved, and such amplitude is determined by the relationship of the masses of the applicator means 16 and coupling means 25 which may be made effective to either magnify or reduce the amplitude of the vibrations received from the transducer.

The tool member 16 may be permanently attached to the end of the coupling means 25, for example, by brazing, solder or the like, or the tool may be provided with a threaded stud 34 adapted to be screwed into a tapped hole in the end of coupling means 25 for effecting the rigid connecting of the tool to the stem. A base portion 35 is provided from which the stud 34 extends, from one end thereof, and from the other end a body 36 which is firmly secured thereto for the transmission of the ultrasonic vibrations. The body portion 36 may be formed with, brazed or welded to, the base 35 of the tool member 16. At the opposite end of the body portion 36 is a head portion or section 40 which is mechanically joined to the body portion 36 such that the mechanical vibratory energy is transmitted therethrough with a component of vibration normal to the surface of the skin 55 as indicated by arrow 38 in FIG. 2.

As seen somewhat schematically in FIG. 2, the biological organism 12, such as a human, contains a layer of outer tissue or skin 42, comprised essentially of dead cells and a layer of malpighian cells 44 which together form the epidermis layer. A foreign deposit 45, as seen in FIGS. 3-5, such as a blackhead, is contained in a pocket or cavity 46 in the skin contained at a work or removal site 49.

The applicator means 16 has an output edge 20 and a spaced apart input or rear end 48 with a conical side wall 50 extending therebetween such that the output edge 20 has an aperture or opening 52 to permit the blackhead or other foreign deposit 45 to be removed from the cavity 46 in which it is situated or contained.

The fluid supply means 30 is in communicating relation to the instrument means 14 through conduit 27 and in turn is connected to a tubular member 51 longitudinally extending in the casing 24 with respect to the motor 15. The tubular member 51 is connected to the coupling means 25 and in axial alignment with a duct 53 that is communicating with a passage 56 that extends through the threaded stud 34 and in turn through the body portion 36 and terminating at an orifice or aperture 57 at the inner surface 59 of wall 50 of the head portion 40. In this manner the fluid 39 exits within the confines of the body portion 40 at or adjacent the work site 49 such that the fluid 39 may form a layer on the tissue surface 55. The fluid 39 may be cavitated due to the vibratory motion of the tool 16 such that a fine mist or spray is obtained. The fluid supply means 30 may be operated simultaneously with the generator means 26, or the fluid supply means 30 may first be activated to coat the tissue surface 55 with the fluid medium 39.

THEORY OF PRESENT INVENTION AND OTHER EMBODIMENTS

Whereas a scientific explanation of the theory based on the phenomena involved is disclosed below, it is to be clearly understood that the invention is by no means limited by any such scientific explanation.

Applicants have now discovered that mechanical vibrations properly applied may produce a friction reduction between the foreign deposit and the tissue in surrounding relation thereto. With respect to a pimple the mechanical vibrations effect a rupturing or opening of the tissue surrounding it to permit a release thereof.

For purposes of illustration, we have in FIGS. 3, 4, and 5 a single blackhead 45 having a cavity 46 with a wall surface 54 contacting the outer wall of the blackhead 45 which for purposes of illustration is seen to be substantially flush with the tissue surface 55 proximate thereto.

At the interface of the contacting surface of the output edge 20 and the tissue surface 55 we have a transmission of both a static force and mechanical vibrational energy to the tissue surface 55 and a localized friction reduction between the cavity wall 54 and the outer wall 47 of blackhead 45.

The magnitude of friction reduction between the contacting surface of the output edge 20 and the tissue surface 55 is in part related to the actual amplitude of vibration. As seen in FIG. 6, the contacting surface of the output edge 20 is moving from between the solid line, at one end of a vibratory cycle, to the phantom surface line at the other end of the vibratory cycle, approximately 20,000 cycles per second, at say an amplitude of vibration of 0.002 inch. This essentially means that the output edge 20 is continuously moving away from the tissue surface 55 at a quicker rate than the gravitational force of gravity such that in a sense only upon the contacting surface of the output edge 20 reaching its peak height is it momentarily in contact with the tissue surface 55. This phenomenon is a unique property of ultrasonic vibratory mechanical energy which can be utilized to apply high frequency mechanical vibrations with a minimum of heat buildup.

It has been found that, by reason of the vibrations in a plane perpendicular to the direction of the static force, the frictional resistance is very substantially reduced. A possible explanation of this observed phenomenon is that the extremely high acceleration of the contacting surface results in the vibrations transmitting only a relatively small amount of friction to be present between the contacting output edge surface 20 and the tissue surface 55. In addition to having a component of vibration normal to the tissue surface 55, the output edge 20 may also have torsional, elliptical, flexural modes of vibration as well.

Static pressure or force is exerted on the tissue surface 55 by the pressure of the user 22. As illustrated in FIG. 6, the frequency of the vibrations between the solid and phantom line at a zone of motion at the output edge or free end portion 20 of the applicator means 16 may be in the range from 10 to 100 kilocycles per second and preferably in the range from 20 to 80 kilocycles per second, while the amplitude of the vibrations is selected within the range from approximately 0.0005 to 0.025 inch so as to ensure the introduction of vibratory energy sufficient to substantially minimize the frictional resistance of the blackhead 45 to the cavity 46.

The contacting surface of the output edge 20 may vibrate at 20,000 cycles per second a distance longitudinally approximately 0.002 inch, or say in the range of 0.002–0.003 inches. This vibration achieves peak acceleration of about 41,000–62,000g and forms the zone of motion which is essentially impenetrable by the tissue. The actual contact of the tissue 55 with the contacting surface 20 is for only a small portion of each cycle of vibration.

Accordingly, suppose the contacting surface 20 has a peak stroke of 0.004 inch, then it would reach a peak acceleration of 82,000g. So, in the first instance we see that the output is relatively low speed 21 ft/sec. which is approximately 14 miles/hour. But the peak acceleration exceeds anything that can be achieved in any other way by mechanical means at such low speed.

Therefore, one of the first discoveries about the vibrating surface is that its peak output speeds are very safe, while at the same time extraordinarily high accelerations are utilized. An immediate consequence of this fact is that for bodies moving with accelerations of say 1 g; i.e., the human tissue on the contacting surface, there will be very little penetration of the zone of motion. For example, suppose the skin tissue surface 55 is in contact with the contacting output edge surface 20 at the end of a stroke and is capable of moving into the zone of motion with an acceleration of one g. Then the contacting surface will retract a distance, S, and return the same distance in a time equal to one period of oscillation of the motor. Since, for 20,000Hz this period is 50 microseconds, we can calculate how far a 1 g accelerated body, the skin tissue surface 55, can move in 50 microseconds, starting from rest. This we get from the simple equation:

| | |
|---|---|
| d = distance travelled | $d = \frac{1}{2} st^2$ |
| a = acceleration due to gravity, "g" | $d = .483 \times 10^{-6}$ in. |
| t = time | $s = .004$ in. $= 4 \times 10^{-3}$ in. |
| s = stroke | $d/s = .012 \times 10^{-2}$ or .012% |

Thus, d/s, which measures the penetration of the zone of motion amounts to less than 0.012%. Accordingly, even if the tissue is moving toward the contacting surface with an acceleration of one g, the space penetration is less than 0.012%.

Thus, the skin moving with such a vibrating surface would be in contact with the surface for less than 0.012% of the time. This means that there is essentially an air-borne film between the contacting surface and the tissue while at the same time large dynamic forces are applied to produce the movement of the blackhead relative to the cavity wall thereof.

If the foreign deposit is a pimple, then the same procedure is carried out and the static force of the applicator means against the surface of the skin is maintained until a rupture of the tissue surrounding the pimple occurs.

To aid in coupling the vibration energy to the skin, the fluid medium 39 may be first applied to the skin adjacent the foreign object at the work site 49 to be removed for engagement with the output edge 20. The amplitude of vibration may be such as to produce a cavitational action in the fluid medium 30 which may consist of a commercially known form.

Although it was initially believed that the natural oils in the skin would serve as a good coupling medium between the instrument head and the tissue, it has been found that it was most important to provide a fluid medium to the work site. Accordingly, in accordance with the present invention a thin film or spray of suitable material not harmful (even beneficial) to skin is applied prior to, simultaneously with, or during the application of the ultrasonic mechanical vibrations. The fluid medium 30 may be selected for a variety of purposes to aid the process described above. The fluid medium 30 may be applied locally to the removal site 49 and may be an anaesthetic solution in order to numb any sensations from the transmission of vibratory energy to the tissue surface 55. The fluid medium 30 may also be in the form of an antiseptic or a combination of an antiseptic and an anaesthetic to both sterilize and temporarily numb the tissue surface 55. By providing a fluid medium 30, it may also aid in coupling the energy. The importance of having an antiseptic solution is that upon the removal of the foreign deposit 45, the antiseptic fluid medium would flow into the cavity 46 such that any germs contained therein would be destroyed thereby preventing infection to take place within the cavity 46.

Further, the fluid medium may also include cold creams, vaseline, and other skin creams and lotions. In the case of using a cream or lotion as the fluid medium, an additional benefit of skin treatment occurs in the vicinity of the applicator means 16 due to activation and better penetration of the cream or ointment into the skin or tissue surface 55. Also, the benefits of local stimulation by micro-massage is also present in accordance with the present invention and is not present in conventional methods.

The fluid supply means 30 may contain more than one fluid medicament if desired and in the embodiments illustrated in FIGS. 2-6 previously described, and in FIGS. 7-16 to be hereinafter described, the fluid is supplied to the work site 49 through the applicator means 16. The fluid may be delivered to the work site 49 in more than one direction and externally of the applicator means 16 as hereinafter described with respect to the embodiment illustrated in FIG. 17.

FIGS. 7-10 illustrate a form of applicator means 16a, which may be made of a metallic or plastic material and either formed out of one piece or manufactured out of several pieces in accordance with conventional manufacturing procedures. The applicator means 16a includes a base portion 35a that may have a circular, square, or hexagonal cross sectional area, the latter two permitting ease in securement of the applicator means 16a via threaded stud 34a to the instrument means as illustrated in FIG. 2.

Extending from the front end 58a of the base section 35a is a body portion 36a that is seen in FIG. 8, is tapered from its rear section that is coupled to the front section 58a and tapers downwardly to the head portion 40a, secured at the opposite end. As seen in FIG. 7, the body portion 36a has an upper arm 60a angularly disposed with respect to the base portion 35a and a lower arm 62a that is angularly disposed in an opposite direction and which has the head portion 40a secured thereto. The head portion 40a has an output edge or surface 20a at one end thereof and a rear surface or edge 48a spaced apart with respect thereto. The output diameter and the wall thickness of the wall 50a is such as to define an aperture or opening 52a at the output edge 20a which opening is of sufficient cross sectional area or diameter to encompass the blackhead and permit its passage therethrough. The fluid passage 56a extends axially through the stud 34a, base section 35a, body portion 36a and terminates in an aperture 57a extending in the side wall 50a and terminating on the inner surface 59a.

As seen, particularly in FIGS. 9 and 10, the head portion 40a has a conical shape in that the output edge 20a has the opening 52a extending thereat with the rear or input end 48a in spaced relation thereto with the side wall 50a tapering therebetween, having the aperture 57a extending therethrough. The head portion 40a has a bottom wall 66a through which the opening 52a extends and which may be thicker or thinner than the side wall 50a.

Once the applicator means 16a is secured to the instrument means, the vibrational energy will be transmitted thereto since the material of which it is constructed is capable of supporting and transmitting high frequency mechanical vibrational energy in the manner to transmit said energy to the contacting suface of the output edge 20a in a prepared manner for application to the skin of the user. The amplitude of vibration is selected to produce a quantitative reduction of friction between the foreign deposit and the tissue in surrounding relation thereto to aid in effecting a displacement therefrom. The contacting surface 20a circumferentially aplies a static force to the tissue in surrounding relation to the foreign deposit being removed and simultaneously conforms to the contour of the skin.

FIGS. 11-13 illustrate another form of the present invention where applicator means 16b is of different configuration and which consists of a head portion 40b, which may be made of plastic, at one end thereof and a base portion 35b having a hexagonal shape to permit its ready securement via the threaded stud 34b that extends therefrom. The body portion 36b joins together with the base section 35b and head portion 40b. The body portion 36b may have a stud (not shown) extending axially therein from the base portion 35b to obtain proper securement and transmission of vibratory energy therethrough. The head portion 40b is at an angle with respect to the vertical direction of the axis of the body portion 36b.

As seen more particularly in FIGS. 12 and 13, the head portion 40b has an output edge 20b at one end thereof and an input end 48b at its opposite spaced apart end with an opening extending therebetween such that at the lower end we have a bottom wall 66b which has a conical or hourglass shape tapering inwardly from the output end 20b as defined by an axially extending cavity wall surface 54b which mates with cavity wall surface 68b and in turn with outwardly tapering cavity wall surface 70b. The cavity 70b thereafter opens to the atmosphere at the rear wall 72b in a pocket or recess 73b that extends to the input end 48b, such that the extracted foreign object may exit through the cavity and the head portion 40b. The outer surface of the head portion 40b may in turn have a front section that may have a curved surface 74b to thereby reduce the cross sectional area as defined by the output edge 20b. The fluid passage 56b extends axially in the stud 34b, base section 35b, then through the body portion 36b, and in turn through the head portion 40b, and terminating in aperture 57b in the cavity wall 54b. Although a single aperture 57b has been illustrated, more than one such aperture may be provided at or adjacent the output end 20b.

Suitable plastic solid materials which are capable of sustaining ultrasonic vibrations without softening in the range needed to practice the invention and, at the same time, having a specific acoustic impedance (density x speed of sound in the plastic = pc) which can approach the corresponding impedance of skin (fleshy tissue) are suitable for use.

As a result of the closer impedance match, considerably more ultrasonic energy flows from the applicator into the matter to be squeezed out for a given static push on the device against the tissue. Thus, it should be possible to introduce significant amounts of coherent vibration into the blackhead or pimple with relatively soft pushing or pressure.

A blackhead removing tool made of Lexan and vibrating at 30KHz with an output stroke of the order of 0.0005 inch (500 microinches), can be used to remove blackheads and express small pimples with great ease and comfort at squeezing forces less than those used in conventional instruments. The amplitude of vibration is preferably in the range of 0.0001 inch to about 0.070 inch, at a frequency in the range of 16,000 cycles per second to 100,000 cycles per second. By providing an aperture or opening 52c, the user of the instrument may selectively position the contacting surface 20c around the foreign deposit.

Now, it is well known that the acoustic impedance of soft tissue (which is mainly water) is about the same as that of water. The following table shows one of the great virtues of Lexan:

| Material | Density pd/m$^3$ | Speed of waves c=ips × 10$^3$ | pc × 10$^3$ acoustic impedance pd/m$^2$ sec | Wave Length (in) at 30 KHz |
|---|---|---|---|---|
| Lexan | .043 | 56.1 | 2.02 | 1.87 |
| Water | .036 | 59.0 | 2.12 | 1.97 |

The table shows that Lexan and water are closely matched in acoustic impedance and, hence, the transfer of vibration energy into tissue (which closely matches water in acoustic impedance) is facilitated. The magnitude of the effect may be appreciated when it is realized that the corresponding values of acoustic impedance for acoustically usable metals may be anywhere from ten to thirty times the acoustic impedance of the soft tissue.

Figure 14:
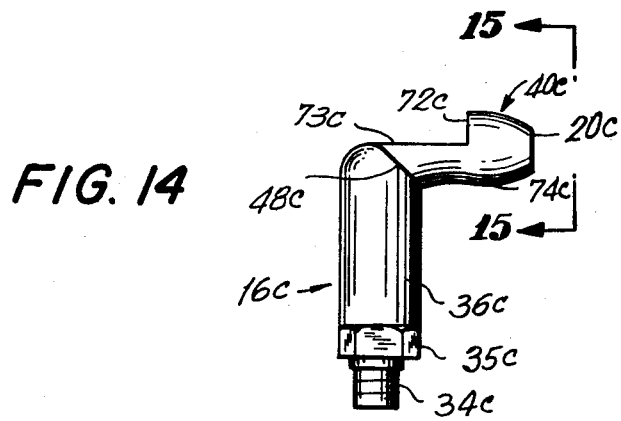
FIG. 14 is a view similar to FIG. 7 illustrating another form of applicator means.
Figure 16:
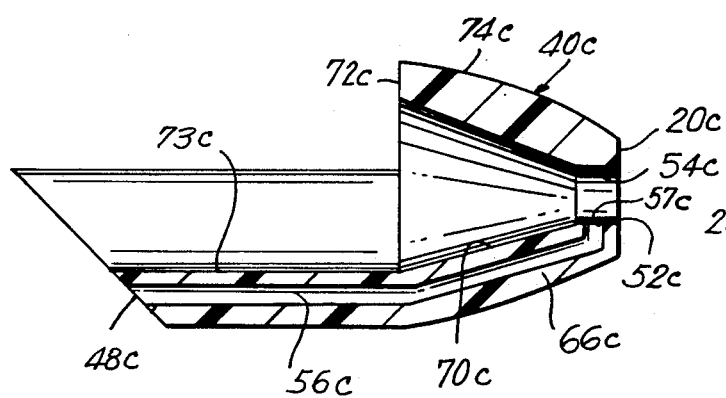
FIG. 16 is a an enlarged sectional view of a portion of said applicator means taken along the line 16—16 of FIG. 15.
Figure 15:
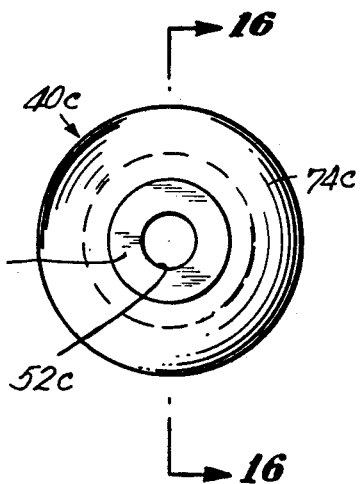
FIG.15 is an enlarged partial end view taken along the line 15—15 of FIG. 14.

FIGS. 14–16 illustrate another form of the applicator means 16c for which the head portion 40c is in effect at right angle with respect to the body portion 36c which has a base portion 35c and threads 34c extending therefrom. The head portion 40c is basically similar to the head portion illustrated in FIGS. 12 and 13 in that we have an output edge 20c and spaced apart input end 48c with a bottom wall 66c connected by an axially extending opening 52c which includes a cavity wall surface 54c that merges with an outwardly tapering portion 74c and terminating in part at the wall 72c to permit the removal of the foreign deposit from the skin of the user. The rear wall 72c terminates in a pocket 73c that extends to the input end 48c. An external curved surface 74c may be provided. The fluid passage 56c extends axially in the stud 34c, base section 35c, then through the body portion 36c and in turn through the head portion 40c and terminating in aperture 57c in the cavity wall 54c. The applicator 16c may be of a metallic or plastic material.

Figure 17:
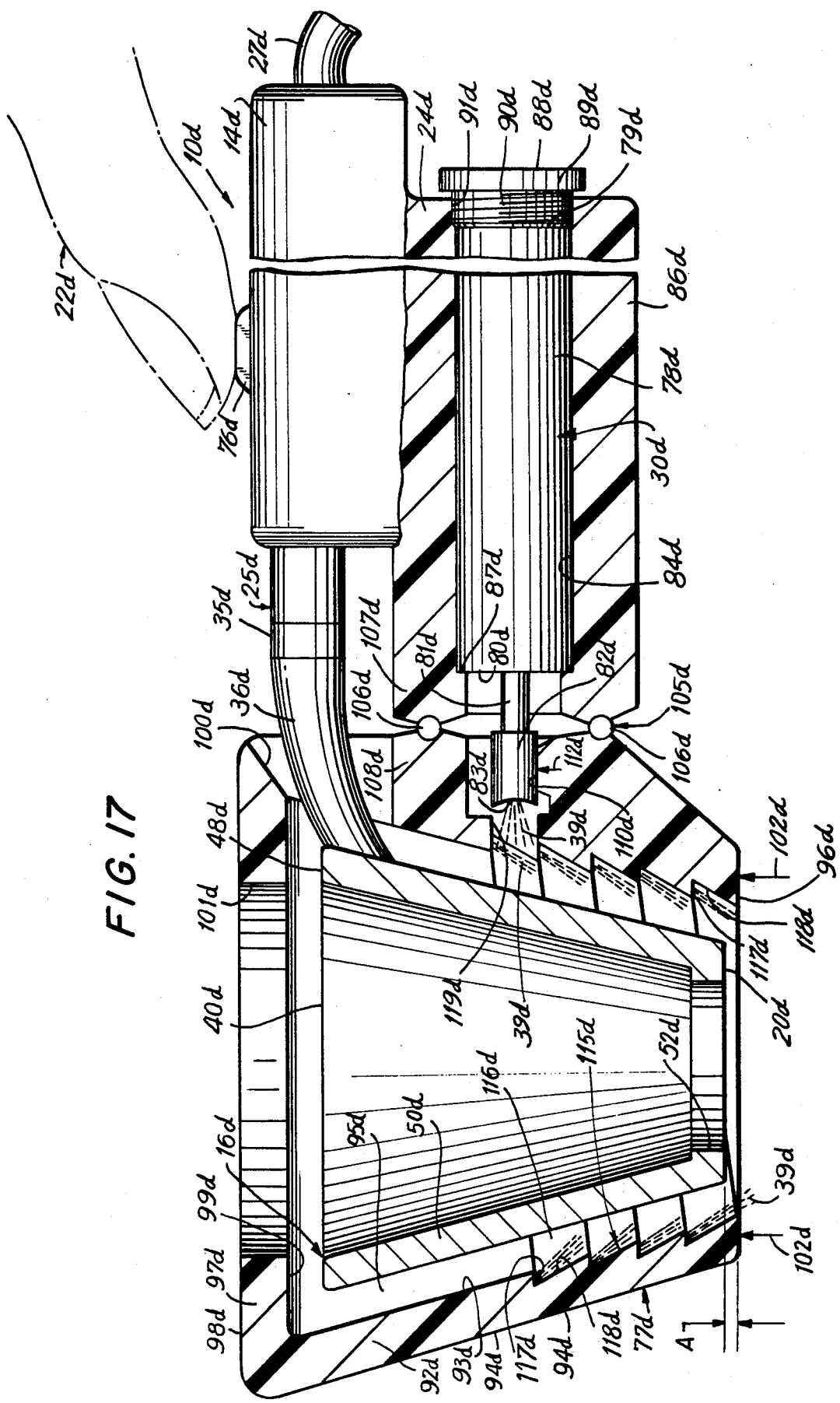
FIG. 17 is an enlarged fragmentary section illustrating another form of the invention.

FIG. 17 illustrates another embodiment of the present invention in which the instrument means 14d is adapted to be hand held and provides the feature of having an on and off switch 76d that may be activated manually by the operator 22d. In certain instances it is desirable to be able to initially position the contacting surface 20d of the head portion 40d of the applicator means 16d in position prior to having the electrical energy through the conduit 27d vibrate the ultrasonic motor contained in the housing 14d and transmitted via coupling means 25d to the base portion 35d and in turn to the body portion 36d.

An additional feature of the embodiment in FIG. 17 is that the fluid 39d is supplied externally of the applicator means 16d. To accomplish this there is provided fluid delivery or transporting means 77d that is mounted in telescopic relation to the applicator means 16d and may be constructed in one or more pieces to be assembled in surrounding relation thereto. The fluid delivery means is mounted in operative relation to the fluid supply means 30d which in this embodiment is illustrated in the form of a replaceable reservoir 78d having a rear end 79d, a front end 80d with an axially extending valve stem 81d extending from the front end 80d and terminating in a valve 82d which when activated will release therefrom the fluid 39d from the front orifice at the upper end 83d of the valve 82d. The reservoir 78d may be a pressurized cannister that is mounted within a cavity 84d extending within a downwardly extending enlarged portion or neck 86d of the housing means 14d and forming part of the casing 24d.

The reservoir 78d may be returned by a shoulder 87d against which the front end 80d rests with a removable closure or cap 88d having portion 89d and a threaded section 90d that mates with complementary threads 91d at the rear end of the cavity 84d. The user of the instrument 10d will insert the dispenser 78d within cavity 84d and tighten the cap 88d until the front end 80d is brought into fixed relation with the annular shoulder 87d.

The fluid delivery means 77d includes a side wall 92d that extends at substantially the same inclined angle or taper as the side wall 50d having an inner surface 93d and an outer surface 94d. The annular spacing between the inner surface 93d and the outer surface of the wall 50d provides a passageqay 95d for the fluid 39d to be transmitted in the direction of the output end 20d. The fluid delivery means 77d terminates in a front end 96d that extends in a plane substantially parallel to the contacting surface 20d. A hood portion 97d may be integrally formed with the wall 92d and having an outer or top surface 98d and an inner surface 99d in spaced relation to the rear surface 48d of the head portion 40d. An opening 100d to permit the body portion 36d access therethrough is provided in the wall 92d. A viewing aperture 101d is provided in the hood 97d in substantially coaxial alignment with the opening 52d which terminates at the contacting surface 20d. The opening or aperture 52d may be of cross sectional diameter in the range of 0.030 inch to 0.250 inch, but generally in the range of approximately 0.060 inch.

The viewing aperture 101d permits the user of the instrument 10d, or someone else using the instrument 10d, to properly position the front end 96d against the skin such that a responsive static or compressive force in the direction of arrows 102d is obtained.

To facilitate ease of operation and to be assured that a supply of fluid 39d is maintained at the removal site, there is provided automatic activating means 105d that will activate the valve 81d so that the fluid 39d flows into the passageway 94d and to the work site adjacent the contacting surface 20d. The automatic means 105d includes a hinge 106d mounted between the forward end 107d of the downwardly extending portion 86d and the outwardly extending rear wall portion 108d of the fluid delivery means 77d. A shoulder 110d abuts the valve 82d and applies a force in the direction of arrow 112d.

As seen in FIG. 17, a spacing defined by dimension A is provided between the output end 96d and the contacting surface 20d. In operation when the output surface 96d is applied against the skin and the force in the direction of arrows 102d is applied thereto, the shoulder 110d engages the valve 81d, and sufficient movement of the valve 81d occurs to permit a release of the fluid 39d contained therein. The hinge 106d may be integrally formed or mounted as illustrated and may be of a compressive material to permit the angular displacement of the fluid delivery means 79d required to open the valve 81d, and thereafter upon disengagement of the front surface 96d the valve 81d returns to its normally closed position.

To properly assure the flow of fluid 39d in the proper direction, delivery or channel means 115d is provided in operative relation with the inner wall 93d and passageway 95d. The channel means 115d may include a continuous downwardly extending series of grooves 116d having an upper end 117d and an inclined wall 118d. The grooves may extend in a helix or spiral to in effect obtain a flow of the fluid 39d towards the contacting surface 20d in order to assure a proper delivery of fluid 39d for use with the instrument 10d. If desired the grooves may be provided on the exterior surface of the head portion 40d to obtain an ultrasonic pumping action. Opening 119d is in alignment with the valve upper end 83d and the channel means 115d to permit the fluid 39d to enter the passageway 95d. The fluid delivery means 77d may be used in conjunction with the other applicator means illustrated with respect to FIGS. 7–16.

The relative width of the contacting surface 20d also pressurizes the fluid 39d for enhancing the effectiveness of the removal of the foreign deposit from the skin. It is appreciated that the reservoir 78d may be positioned as illustrated and activated in conjunction with the finger switch 76d or in some other manner to properly apply the fluid.

CONCLUSION

Although this invention has been discussed primarily with reference to blackheads and pimples, it is to be understood that the invention is not limited thereto or thereby. The process may be used wherever foreign object are required to be removed or ruptured.

Although illustrative embodiments of the invention have been described in detail herein with reference to the accompanying drawings, it is to be understood that the invention is not limited to the precise embodiments, and that various changes and modifications may be effected therein without departing from the scope or spirit of the invention.

I claim:

1. The method of removing a foreign deposit from the tissue of a human comprising the steps of:
   A. positioning adjacent said foreign deposit to be removed a surface capable of supporting and transmitting ultrasonic vibrations,
   B. supplying a fluid to the tissue adjacent said foreign deposit for engagement by said surface,
   C. inducing vibrations in said surface at a frequency in the ultrasonic range,
   D. moving said ultrasonically vibrating surface relative to said foreign deposit such that it substantially engages the tissue and applies a force thereto, whereby an extraction of said foreign deposit from its containment in said tissue is obtained, and
   E. circumferentially applying a static force to the tissue in surrounding relation to said foreign deposit.

2. The method of removing a foreign deposit from the tissue of a human comprising the steps of:
   A. positioning adjacent said foreign deposit to be removed a surface capable of supporting and transmitting ultrasonic vibrations,
   B. supplying a fluid to the tissue adjacent said foreign deposit for engagement by said surface,
   C. inducing vibrations in said surface at a frequency in the ultrasonic range,
   D. moving said ultrasonically vibrating surface relative to said foreign deposit such that it substantially engages the tissue and applies a force thereto, whereby an extraction of said foreign deposit from its containment in said tissue is obtained, and
   E. substantially conforming the contour of said surface for engagement with the tissue.

3. The method of removing a foreign deposit from the tissue of a human comprising the steps of:
   A. positioning adjacent said foreign deposit to be removed a surface capable of supporting and transmitting ultrasonic vibrations,
   B. supplying a fluid to the tissue adjacent said foreign deposit for engagement by said surface,
   C. inducing vibrations in said surface at a frequency in the ultrasonic range,
   D. moving said ultrasonically vibrating surface relative to said foreign deposit such that it substantially engages the tissue and applies a force thereto, whereby an extraction of said foreign deposit from its containment in said tissue is obtained, and
   E. providing an aperture in said surface adapted to be selectively positioned around said foreign deposit.

4. The method as defined in claim 1, wherein said surface is comprised of a plastic material.

5. The method as defined in claim 1, wherein said surface is comprised of a metallic material.

6. The method as defined in claim 1, and further including the step of vibrating said surface at an amplitude of vibration to produce a quantitative reduction of friction between said foreign deposit and the tissue in surrounding relation thereto to effect a displacement therefrom.

7. The method as defined in claim 1, wherein said surface is vibrated in the frequency range of 1,000 cycles per second to 1,000,000 cycles per second.

8. The method as defined in claim 7, wherein said frequency is preferably in the range of 16,000 cycles per second to 100,000 cycles per second.

9. The method as defined in claim 1, wherein the amplitude of vibration of said surface is in the range of 0.0001 inch to about 0.070 inch.

10. The method as defined in claim 1, and further including the step of continuously supplying a stream of said fluid to the tissue.

11. The method as defined in claim 10, and further including the step of pulsing said surface at a preselected pattern of pulses at spaced intervals of time in the frequency range of up to 1,000 cycles per second.

12. The method of removing a foreign deposit from the tissue of a human comprising the steps of:
   A. positioning adjacent said foreign deposit to be removed a surface capable of supporting and transmitting ultrasonic vibrations, said foreign deposit is a blackhead,
   B. supplying a fluid to the tissue adjacent said foreign deposit for engagement by said surface,
   C. inducing vibrations in said surface at a frequency in the ultrasonic range, and
   D. moving said ultrasonically vibrating surface relative to said foreign deposit such that it substantially engages the tissue and applies a force thereto, whereby an extraction of said blackhead from its containment in said tissue is obtained.

13. The method of removing a foreign deposit from the tissue of a human comprising the steps of:

A. positioning adjacent said foreign deposit to be removed a surface capable of supporting and transmitting ultrasonic vibrations, said foreign deposit is contained within a pimple,
B. supplying a fluid to the tissue adjacent said foreign deposit for engagement by said surface,
C. inducing vibrations in said surface at a frequency in the ultrasonic range, and
D. moving said ultrasonically vibrating surface relative to said foreign deposit in said pimple such that it substantially engages the tissue and applies a force thereto, whereby an extraction of said foreign deposit from its containment in said pimple is obtained.

14. The method as defined in claim 1, wherein said fluid is an antiseptic to maintain a sterilized condition.

15. The method as defined in claim 1, wherein said fluid is an analgesic.

16. The method as defined in claim 1, wherein said fluid is a lotion.

17. The method as defined in claim 1, and further including the step of regulating the rate of supplying said fluid.

18. The method as defined in claim 1, and further including the step of controlling the amplitude of vibration of said surface by regulating the electrical power delivered thereto.

19. The method of removing a foreign deposit from the skin of a human comprising the steps of:
A. providing an applicator having a contacting surface capable of supporting and transmitting ultrasonic vibrations,
B. positioning said contacting surface adjacent said foreign deposit to be removed for transmitting to the skin mechanical vibratory energy in the ultrasonic frequency range,
C. supplying a fluid to the tissue adjacent said foreign deposit for engagement by said contacting surface,
D. vibrating said contacting surface at an ultrasonic rate to produce peak accelerations of at least 1,000g, and
E. moving said ultrasonically vibrating contacting surface relative to the skin in a direction such that it engages the skin and said foreign deposit is released therefrom.

20. The method as defined in claim 19, wherein said contacting surface is vibrated in a plane substantially normal to the skin.

21. The method as defined in claim 19, and further including the step of providing said applicator with an aperture contained therein, and said aperture is placed in surrounding relative to said foreign deposit.

22. The method as defined in claim 21, wherein said foreign deposit exits through said aperture.

23. The method as defined in claim 19, wherein said foreign deposit is a blackhead.

24. The method as defined in claim 19, and further including the step of maintaining a compressive force by said contacting surface against the skin until a rupture of the tissue surrounding said foreign deposit occurs.

25. The method as defined in claim 24, wherein said foreign deposit is a pimple.

26. The method as defined in claim 19, and further including the step of periodically vibrating the contacting surface at a sonic frequency in the range of 10 cycles per second to 1,000 cycles per second.

27. The method as defined in claim 26, wherein said frequency is preferably in the range of 1,000 cycles per second to 100,000 cycles per second.

28. The method as defined in claim 19, and further including the step of retracting said contacting surface from engagement with the skin upon release of said foreign deposit therefrom.

29. The method as defined in claim 19, wherein said fluid is a medicament.

30. The method as defined in claim 29, wherein said fluid is an antiseptic to maintain a sterilized condition.

31. The method as defined in claim 29, wherein said fluid is an analgesic.

32. The method as defined in claim 19, wherein said fluid is a lotion.

33. The method as defined in claim 19, and further including the step of regulating the rate of supplying said fluid.

34. The method as defined in claim 19, wherein said contacting surface is vibrated in the frequency range of 1,000 cycles per second to 1,000,000 cycles per second.

35. The method as defined in claim 19, and further including the step of continuously applying said fluid to the skin adjacent said foreign deposit for engagement by said contacting surface, as said applicator is ultrasonically vibrated.

36. The method as defined in claim 19, and further including the step of first applying a compressive force in a plane substantially normal to the skin with said contacting surface prior to vibrating same.

37. The method as defined in claim 36, and further including the step of automatically supplying said fluid when said contacting surface engages the skin and a compressive force is applied.

38. The method as defined in claim 19, and further including the step of supplying said fluid through said applicator.

39. The method as defined in claim 19, and further including the step of supplying said fluid externally of said applicator.

40. The method as defined in claim 19, and further including the steps of:
a. providing said applicator with an aperture contained therein, and said aperture is placed in surrounding relation to said foreign deposit,
b. applying said fluid to the skin adjacent said foreign deposit for engagement by said contacting surface, as said applicator is ultrasonically vibrated, and
c. retracting said contacting surface from engagement with the skin upon release of said foreign deposit therefrom.

41. The method as defined in claim 40, and further including the steps of:
a. maintaining a compressive force by said contacting surface against the skin until said foreign deposit is released, and
b. automatically supplying said fluid when said compressive force is initially applied.

42. Apparatus for removing foreign deposits from the skin, comprising:
A. applicator means having a contacting surface thereon capable of supporting and transmitting ultrasonic vibrations,
B. means operatively associated with said applicator means for supplying a fluid to the skin adjacent said foreign deposit, C. means for inducing vibrations in said applicator means such that said contacting surface is vibrated at a frequency in the ultrasonic range, and
D. an aperture on said contacting surface, such that as said contacting surface is moved into engagement with the skin said foreign deposit is removed from the skin and through said aperture means.

43. Apparatus as defined in claim 42, wherein said applicator means is in the form of a member having a head portion at one end thereof with said aperture extending through said head portion.

44. Apparatus as defined in claim 42, wherein the cross sectional area of said aperture is dimensioned to encompass said foreign deposit to be removed from the skin.

45. Apparatus as defined in claim 42, wherein said motion of said contacting surface is of an amplitude of vibration to produce peak accelerations of at least 1,000g.

46. Apparatus as defined in claim 42, wherein said contacting surface is vibrated in the frequency range of 1,000 cycles per second to 1,000,000 cycles per second.

47. Apparatus as defined in claim 46, wherein said frequency is preferably in the range of 16,000 cycles per second to 40,000 cycles per second.

48. Apparatus as defined in claim 42, wherein the amplitude of vibration of said contacting surface is in the range of 0.0001 inch to about 0.070 inch.

49. Apparatus as defined in claim 42, and further including means for pulsing said ultrasonic energy at a preselected pattern of pulses at spaced intervals of time in the frequency range of up to 1,000 cycles per second.

50. Apparatus as defined in claim 42, wherein said applicator means is of a plastic material.

51. Apparatus as defined in claim 42, wherein said applicator means is of a metallic material.

52. Apparatus as defined in claim 42, wherein said applicator means includes a contoured output edge.

53. Apparatus as defined in claim 42, wherein said applicator means includes a head portion at one end thereof and a base portion at the opposite end thereof with said base portion adapted to be removeably secured to said means for inducing vibrations.

54. Apparatus as defined in claim 53, wherein said aperture extends axially through said head portion and includes an outwardly extending cavity wall surface tapering outwardly from said aperture.

55. Apparatus as defined in claim 53, wherein said head portion is angularly disposed relative to said base portion.

56. Apparatus as defined in claim 53, wherein said head portion is angularly disposed at an angle of approximately 90° to said base portion.

57. Apparatus as defined in claim 53, and further including threaded means at one end of said base portion for removeably securing said applicator means.

58. Apparatus as defined in claim 42, wherein said fluid is supplied through said applicator means.

59. Apparatus as defined in claim 42, wherein said fluid is supplied externally of said applicator means.

60. Apparatus as defined in claim 42, and further including means for automatic supply of said fluid when said contacting surface engages the skin and a compressive force is applied.

61. Apparatus as defined in claim 60, and further including means to channel said fluid to said contacting surface.

62. Apparatus as defined in claim 42, and further including control means operatively associated with said fluid supply means for regulating the amount of flow therethrough.

63. Apparatus as defined in claim 42, and further including fluid reservoir means adapted to be readily positioned in operative relation to said means for supplying said fluid.

64. Apparatus as defined in claim 42, wherein said means for inducing vibrations in said applicator means includes:
 a. motor means mounted in a housing adapted to be hand held, and
 b. a generator for converting electrical current to said ultrasonic range.

65. Apparatus as defined in claim 42, wherein said vibrated contacting surface pressurizes said fluid for enhancing the effectiveness of the removal of said foreign deposit from the skin.

66. Apparatus as defined in claim 65, wherein said fluid is cavitated.

67. Apparatus for removing foreign deposits from the skin, comprising:
A. applicator means having a head portion with a contacting surface and a base portion at the other end thereof, said applicator means capable of supporting and transmitting ultrasonic vibrations,
B. means for inducing vibrations in said applicator means at a frequency in the ultrasonic range up to 100,000 cyles per second and to produce motion in said contacting surface of an amplitude of vibration to produce peak accelerations of at least 1,000g.
C. means operatively associated with said applicator means for supplying a fluid to the skin adjacent said foreign deposit, and
D. an aperture on said contacting surface extending axially within said head portion and including an outwardly extending cavity wall surface tapering outwardly from said aperture through said head portion, such that as said contacting surface and the skin are moved into engagement with each other, the foreign deposit is removed from the skin and into said aperture.

68. Apparatus as defined in claim 67, wherein said head portion is angularly disposed relative to said base portion.

69. Apparatus as defined in claim 67, wherein the cross sectional area of said aperture is dimensioned to encompass the foreign deposit to be removed from the skin.

70. Apparatus as defined in claim 69, wherein said aperture extends through said head portion and the foreign deposit is viewable therethrough to assist in positioning said applicator means on the skin.

71. Apparatus as defined in claim 67, wherein said fluid is supplied through said applicator means.

72. Apparatus as defined in claim 67, wherein said fluid is supplied externally of said applicator means.

73. Apparatus as defined in claim 67, and further including means for automatic supply of said fluid when said contacting surface engages the skin and a compressive force is applied.

74. Apparatus as defined in claim 73, and further including means to channel said fluid to said contacting surface.

75. Apparatus as defined in claim 67, and further including control means operatively associated with said fluid supply means for regulating the amount of flow therethrough.

76. Apparatus as defined in claim 67, and further including fluid reservoir means adapted to be readily positioned in operative relation to said means for supplying said fluid.

77. Apparatus as defined in claim 67, wherein said applicator means is of a plastic material.

78. Apparatus as defined in claim 67, wherein said applicator means is of a metallic material.

79. Apparatus as defined in claim 67, wherein said means for inducing vibrations in said applicator means includes:
 a. motor means mounted in a housing adapted to be hand held, and
 b. a generator for converting electrical current to said ultrasonic range.

* * * * *